United States Patent [19]

Torev

[11] 4,212,947
[45] Jul. 15, 1980

[54] METHOD FOR OBTAINING MYCELIUM FROM THE GENUS POLYPORUS

[75] Inventor: Atanas K. Torev, Plovdiv, Bulgaria

[73] Assignee: DSO "HRANMASH", Stara Zagora, Bulgaria

[21] Appl. No.: 878,959

[22] Filed: Feb. 17, 1978

Related U.S. Application Data

[63] Continuation-in-part of Ser. No. 687,817, May 19, 1976, abandoned.

[30] Foreign Application Priority Data

May 22, 1975 [BG] Bulgaria .................................. 30055

[51] Int. Cl.$^2$ ......................... C12N 1/14; C12R 1/645
[52] U.S. Cl. .................................. 435/254; 426/656; 435/804; 435/911
[58] Field of Search ....................... 195/115, 81, 1, 32; 426/656, 48, 60; 47/1.1; 435/254, 804, 911

[56] References Cited

U.S. PATENT DOCUMENTS

| | | | |
|---|---|---|---|
| 2,850,841 | 9/1958 | Szuecs ..................................... | 47/1.1 |
| 3,097,145 | 7/1963 | Shimazono et al. .................. | 195/62 |
| 3,151,038 | 6/1964 | Gray et al. .............................. | 195/32 |

OTHER PUBLICATIONS

Maslova, "Effect of the Different Sources of Nitrogen on the Growth of Wood—rotting Fungi in Culture", *Chem. Abstracts*, vol. 72, No. 13, p. 115, (1970), abs. No. 63869x.

Robbins et al., "Unidentified Growth Factors for Polyporus schneinitzii", *Chem. Abstracts*, vol. 72, No. 3, p. 221, (1970), abs. No. 11531n.

*Primary Examiner*—Thomas G. Wiseman
*Attorney, Agent, or Firm*—E. Janet Berry; Lawrence Rosen

[57] ABSTRACT

The strains, PS 64-103; PS 24-44; and PB 33-48 are mutation products of the perfect fungi *Polyporus squamosus* and *Polyporus brumalis* and are characterized by the fact that in a liquid nutrient medium they tend to form hiffs, colonies and secondary spores, subdividing in geometric progression with rapid growth which varies in speed, depending on the seeding material ratio in a period of from 6 to 36 hours. The nutrient medium in which the mycelium is developed is quite simple in composition and comprises three components, i.e., 4–5% of molasses; 0.2% of $NH_4NO_3$; 0.12% of $KH_2PO_4$ and 0.04% of vegetable oil as foam suppressant. The strains assimilate from 50 to 60% of a given amount of saccharoses, accumulating to 1 to 1.2% of dry biological mass.

The fungi mycelium can be adapted as a food product and is also used as an additive to various meat and other food products, i.e., sausage, minced meat, soft and smoked cheeses, vegetable canned food, soups, and bread and other bakery products. The waste water stimulates the growth of vegetables.

6 Claims, 1 Drawing Figure

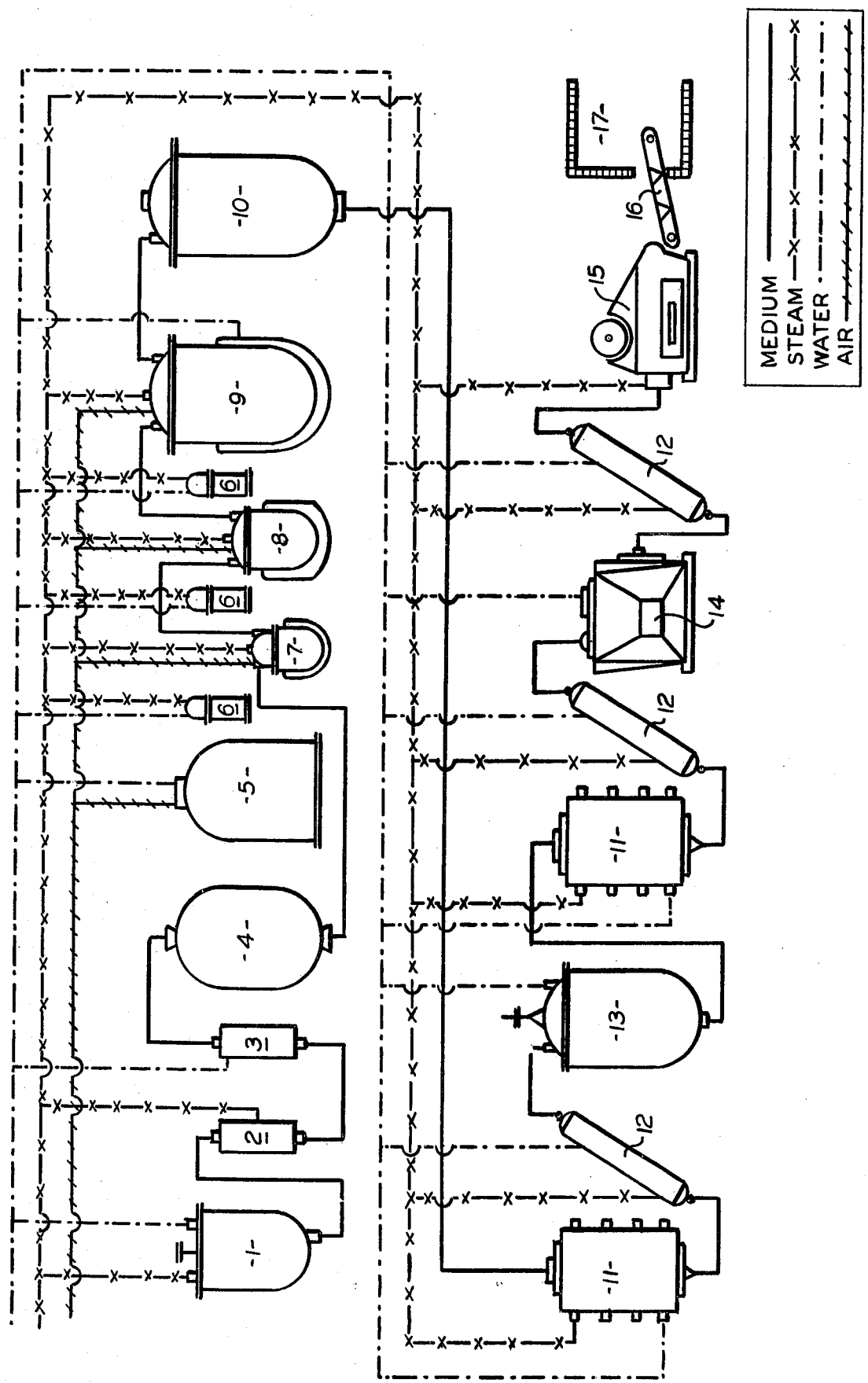

METHOD FOR OBTAINING MYCELIUM FROM THE GENUS POLYPORUS

This application is a continuation-in-part application of copending application Ser. No. 687,817, filed May 19, 1976, abandoned.

The present invention relates to a method for obtaining mycelium from fungi (genus Polyporus) by culturing in depth to give products for foodstuffs having high protein content.

In 1938, for the first time, Lambert (USA) developed a project for cultivating mycelium from fungi for use as foodstuff.

Later Humfeld, Block, Jennison and others carried out tests for cultivating mycelium from *Agaricus cisporus, Morchela esculenta* and other varieties of fungi.

The mycelium from these types of fungi grows for 3 days to a week. The technology suggested by the above authors employs an interrupted method. This technology and the long period of time required for the mycelium to grow have a number of disadvantages:

(1) The required long period of time under sterile production may cause infection of the media by outside microflora and result in obtaining a product of bad quality.

(2) The prolonged growing period prevents advancing to a chain production method.

(3) The product thus obtained is very expensive.

It is a purpose of this invention to teach a method for obtaining mycelium of high food value and rich in protein by cultivating in depth using a chain method under industrial conditions.

The method according to the invention consists in using strains of non-toxic edible high fungis of the genus Polyporus or its variants and mutants for obtaining fungis mycelium of high protein content. The media wherein the fungi mycelium is grown contains as a base, the carbohydrates, both mono and disaccharides. Dairy-production wastes and hydrolysates can also be used. The already used Polyporus strain can be also used. The Polyporus strain used can be *Polyporus squamosus* or *Polyporus brumalis*. *Polyporus squamosus* Hudo strain PS 64 is preferred. The preferred strains and variants of polyporous are deposited in the State Institute of Treatment Means Control, Bulgaria, Sofia, Bl. VI. Zaimov 26, under the numerals PS-64-103; Ps-24-44; and PB-33-48. The following variants can also be used: PS 24-44; PB 33-48. The strain 64-103 is characterized by its very quick growth.

If the quantity of the innoculum is in a ratio 1:1 to the media, the cycle of growth is completed in 7 hours. This strain has the following morphological characteristics: hyphae several millimeters to several centimeters long and 8–10μ thick; on solid media it forms fluffy columns, in liquid media it forms columns with budding hyphae and secondary (vegetative) spores, it propagates only vegetatively through germination and cell divisions and by elongating the hyphae and the colonies. Strain PS 24-44 differs from PS 64-103 only in the thickness of the hyphae 6–8μ and in its more slightly expressed germination. Strain PB 33-48 differs from PS 64-103 only by its longer hyphae, its relatively poor germination, and its inability to produce secondary spores. Strain PS 64-103 grows on nutrient media having mono- and disaccharides. It grows particularly well on nutrient media having glucose and molasses. From all nitrogen salts it absorbs carbamide, ammonium nitrate and ammonium sulfate. From all phosphorus compounds it absorbs potassium and sodium mono- and dibasic phosphate. The growth conditions are temperature, 26° C.±2° C.; pH, 6.5±0.5; air, 0.8±0.2 m$^3$ to each m$^3$ nutrient media per minute. Strain PS 24-44 has the same physiological characteristics as strain PS 64-103. Strain PB 33-48 has the same physiological characteristics as strain PS 64-103. Strain PS 64-103 contains 55–58% raw protein, 42–46% protein, 19–21% carbohydrates, 6–8% cellulose-like substances, and 3–4% fats. If nitrogen is lacking, fats up to 50% can be produced in the nutrient media at the expense of the protein. Total ash is 6–7% and there are present vitamins from the B-complex. Strain 24-44 is characterized by its lower content of raw protein (50–52%) and higher content of cellulose-like substance. Strain PB 33-48 also has a low content of raw protein (48–50%) and a higher content of carbohydrates of about 25%.

Nutrient media for growing the fungus mycelium:

| Solid Nutrient Media | |
|---|---|
| Ingredient | Amount |
| Glucose | 20 g |
| NH$_4$NO$_3$ | 3 g |
| KH$_2$PO$_4$ | 1 g |
| MgSO$_4$ | 0.5 g |
| ZnSO$_4$ | 0.01 g |
| CoCl$_2$ | 0.01 g |
| Agar-agar | 20 g |
| water | 1 liter |

| Liquid Nutrient Media for Innoculum | |
|---|---|
| Ingredient | Amount |
| Glucose | 20 g |
| NH$_4$NO$_3$ | 3 g |
| KH$_2$PO$_4$ | 1 g |
| MgSO$_4$ | 0.5 g |
| ZnSO$_4$ | 0.01 g |
| CoCl$_2$ | 0.01 g |
| water | 1 liter |

| Liquid Nutrient Media for Industrial Production | |
|---|---|
| Beet or red molasses | 5% |
| NH$_4$NO$_3$ 0.15% or carbamide | 0.1% |
| KH$_2$PO$_4$ or NaH$_2$PO$_4$ | 0.1% |
| Sunflower-seed oil as foam-suppressor | 0.03% |

The fungus mycelium is stored on solid substrate as defined for the nutrient media described above. The agar media is poured into Ackerman's test tubes, sterilized at 124° C. for 45 min. and then placed in a tilted position. On agar media the fungus mycelium produces white aerial hyphae of loose structure. It is resown once every six months. It is stored in a refrigerator at +2° C.

The seeding material of liquid substrate is obtained on liquid nutrient media constituted as described above. The media is transferred into Erlenmeyer flasks of 200 ml. each, and the flasks are closed with cotton-lint corks. They are sterilized at 124° C. for 45 min. in an autoclave. They are cooled down to 26° C. and sown in a sterile box, the mycelium having only aerial hyphae or hyphae with part of agar. The test tubes are put in a shaker of 140 revolution per minute in a camera at 26° C. temperature. The period of development is from 72 to 96 hours. The second and third screening takes place from liquid onto liquid media of the same nutrient media and under the same conditions. When sown from liquid onto liquid media for the first time the material takes 60 hours to grow. In the subsequent sowing with sowing material in the ratio of 1:10 the period of growing is about 36 hours.

The liquid nutrient media of the mycelium is stored in a refrigerator at $+2°$ C. for up to 3 months and at $26°$ C. for up to one week.

Sowing Mycelium in an Innoculator

The innoculator can be 1 or 2 $m^3$. It should be washed and sterilized while empty. Then it is loaded with the molasses nutrient media described above up to 80% of its overall volume. The nutrient media is prepared in a media-boiling apparatus, sterilized in sterilization columns and cooled in cooling columns. The innoculator, loaded with nutrient media, is sown sterile with 5 sowing test tubes. The technological regime in the apparatus is t, $26°$ C.$±1°$ C.; pH, $6.5±0.5$; air $0.8±0.2$ $m^3$ in 1 $m^3$ nutrient media for 1 minute without agitation. The pressure in the apparatus is 0.5 atm. $±0.2$ atm. The period of growth of the mycelium is 48 hours.

Intermediate Apparatus Operation

The intermediate apparatus is 15-20 $m^3$. It is washed and sterilized while empty. Then it is loaded with molasses nutrient media, which has been previously sterilized and cooled. The usable volume of the apparatus is 80% (nutrient media with innoculum). It is sown with mycelium from the innoculator through sterile lines. The technological parameters are the same as those for the innoculator stage. It requires the mycelium 24 hours to grow.

Growth of the Mycelium in Working Apparatus

The working apparatus can have a volume of 50-100 $m^3$ or more. The apparatus is washed and sterilized while empty whereupon it is loaded with prepared nutrient media (molasses). The quantity of the nutrient media is calculated so as to occupy 80% of the overall volume of the apparatus together with the sowing material from the intermediate apparatus. The sowing is carried out by using the intermediate apparatus, the mycelium being transplanted on previously sterilized lines. The technological parameters maintained in the apparatus are: temperature, $26°$ C.$±1°$ C.; pH $6.5±0.5$; air, 0.8 $m^3±0.2$ $m^3$ in 1 $m^3$ nutrient media for 1 minute without agitation. The pressure is $0.5±0.2$ atm. The period of growth of the mycelium depends on the quantity of the innoculum. When its ratio to the nutrient media is 1:10 the growth continues for 24 hours. After full growth of the mycelium is reached, half of the cultivation media is passed to filtration and the other half remains as sowing material. The working apparatus is filled again with prepared nutrient media and operating thus, the quantity of the sowing material to the nutrient media is in a ratio of 1:1. Full growth of the mycelium in this case is reached in 6 hours$±1$ hour. Then again half of the cultivation media is pumped out for filtration, fresh nutrient media is added and this process is repeated for 3 days$±2$ days, whereupon everything starts once more from the innoculator and the intermediate apparatus stages. The quantity of fungus mycelium obtained from 1 liter nutrient media is 35 g$±5$ g; 9 g$±1$ g dry (28% dry substance).

Separation of the Fungus Mycelium from the Liquid Phase

Separation is carried out by filtration in filter presses, vacuum drum filters or by centrifugation. The mycelium thus separated is washed with water in the same quantity as the cultivation media filtrate.

The mycelium is divided into solid and liquid phases. The liquid phase (the mother liquor) occupies up to 70% of the cultivation area. The mother liquor is a product having an aqueous base, but also containing substantial quantities of substances from the mycelium metabolism and most important, physiologically active substances having stimulating effects upon plants.

Characteristics of the Final Product

The fungus mycelium can be given two shapes: pressed-fresh and dry.

The pressed mycelium is the fresh mycelium mass containing $28%±1%$ dry matter. Its color is gray-white to light-cream. It has a specific taste similar to the taste of the sour dough. It is obtained in rectangular shape or in the shape of a parallelepipod weighing 5 kg. It is packed in polyethylene wrap and stored frozen at temperatures of $-18°$ C. to $-23°$ C. The product keeps for 6 months. Dry mycelium is obtained by drying in spray driers, air-heated fan driers or boiling-layer driers at $65°$ C.$±5°$ C. The dry mycelium is a flour of coarse or fine particles according to the method of drying. Its color is white to light-cream. It has a specific taste, similar to that of fungus flour. It is poured into double-bottomed paper bags of 25 kg each and stored in a dry airy area at indoor temperature. The product keeps for 1 year.

| Biochemical Characteristics of Strain PS 64-103 Fungus Mycelium | |
|---|---|
| Ingredient | Content |
| Raw protein | 55.8% |
| Pure protein | 45% |
| Carbohydrates (without cellulose) | 21% |
| Fats | 3.6% |
| Cellulose-like substances | 6.4% |
| Mineral composition | 7.0% |
| Thiamin mkg/g | 18.9 |
| Riboflavin mkg/g | 73.0 |
| Niacin mkg/g | 240 |
| Holin mkg/g | 6000 |
| Protein assimilation | 83% |
| Caloricity of 100 g product | 340.16 calories |

The chemical composition of the fungi mycelium is characterized by its high protein content (50-60%) and a complete set of unique amino acids featuring a high lysine content (8-10%). In addition, there are present mycelium "B"-complex vitamins and a number of other physiologically active substances. The protein digestibility is 83%.

With regard to the essential amino acids and digestibility, (i.e. overall biological value) the fungi mycelium almost equals beef meat in value. Thus, the total content of essential amino acids in beef is 39.9% as compared to 39.0% in the mycelium; digestibility of beef is 85% as compared to 83% for the fungi mycelium.

The fungi mycelium obtained from the aforesaid strains was investigated over a period of three years with respect to its effect if any on cancerogen, theratogen and pathomorphological alterations. All results were found to be negative. The tests carried out on the physical and general health effects of the fungi mycelium as a food product have shown that it raises the stamina of organisms, while simultaneously improving the blood condition.

The amino-acid composition of strain PS 64-103 fungus mycelium as compared to the amino-acid composition of beef, casein, soy-bean flour and standard protein according to FAO is shown in Table 1 below. The data are in % relative to the total content of amino-acids.

TABLE 1

|  | Fungus Mycelium P-64 | Beef | Casein | Soy Bean Flour | Standard Protein According to FAO |
|---|---|---|---|---|---|
| Lysine | 8.5 | 8.4 | 8.4 | 6.4 | 5.5 |
| Threonine | 5.3 | 4.0 | 5.0 | 3.8 | 4.0 |
| Valine | 6.0 | 5.7 | 7.4 | 5.0 | 5.0 |
| Isoleucine | 5.1 | 5.1 | 6.2 | 6.4 | 4.0 |
| Leucine | 7.2 | 8.4 | 9.4 | 6.6 | 7.0 |
| Tryptophan | 1.4 | 1.1 | 1.2 | 1.2 | 1.0 |
| Methionine | 1.9 | 2.3 | 2.0 | 0.7 | 3.5 |
| Cystine | 0.9 | 1.4 | 0.3 | — |  |
| Phenylalenine | 3.9 | 4.0 | 5.1 | 4.8 |  |
| Tyrosine | 3.4 | 4.0 | 6.4 | 3.1 | 6.0 |
| Total | 43.6 | 44.4 | 51.4 | 38.0 | 36.0 |
| Histidine | 2.9 | 2.9 | 3.2 | 2.3 |  |
| Arginine | 5.8 | 6.6 | 4.2 | 6.0 |  |
| Aspargic acid | 10.3 | 8.8 | 3.7 |  |  |
| Serine | 4.8 | 3.8 | 6.4 |  |  |
| Glutaminic acid | 16.2 | 14.2 | 22.9 |  |  |
| Proline | 4.0 | 5.4 | 10.9 |  |  |
| Glycine | 4.8 | 7.1 | 2.0 |  |  |
| Alanine | 7.6 | 6.4 | 3.3 |  |  |

A BRIEF DESCRIPTION OF THE FIGURE

The technological process flow diagram for obtaining fungus mycelium is shown on FIGURE wherein the numbers have the following meanings: 1 is the media-boiling apparatus; 2—sterilization columns; 3—cooling columns; 4—container for sterilized nutrient media; 5—total air filter; 6—individual air filter; 7—sowing apparatus; 8—intermediate apparatus; 9—working apparatus; 10—container for cultivation media (developed mycelium); 11—filter presses; 12—screw conveyers or conveyor belts; 13—container for cleaning the mycelium; 14—press machine; 15—molding and packing machine; 16—conveyor belt; 17—cooling chamber.

The Biological Value and Toxicity of the Fungus Mycelium from Fungus (genus Polyporus)

For comparison, a group of rats was used. They were fed with protein from casein and with protein from the fungus mycelium. The comparative results are shown in Table 2 below.

TABLE 2

| Biological Indices | Protein substituted with protein from casein | Protein substituted with protein from fungus mycelium |
|---|---|---|
| Increase in % | 212.6 | 175.2 |
| Digestibility in % | 93.52 | 82.79 |

A blood test has been carried out, the liver has been tested, and also the stomach and the small intestines, and the weight coefficient determined among the inner organs. All the indices are followed up to 7 months. Toxicity or deviation from the acceptable norms have not been observed.

Application of the Fungus Mycelium in the Food Industry

It may be used as an addition of 10 to 20% in meat products (sausages, minced meat for meat-balls, kebapcheta, tinned meat) as a source for obtaining synthetic meat, as an addition to processed and smoked cheeses up to 20%, as an enricher for various tinned vegetables with fungus mycelium up to 25%, in preparing various dry soups (meat and vegetable) in up to 20%; and when preparing bread and other dough products in up to 10%. The following Examples illustrate the application of fungus mycelium in the food industry.

EXAMPLE 1

| Preparation of Perishable Sausages with Fungus Mycelium | |
|---|---|
| Ingredient | Amount |
| Fat Pork | 20% |
| Semi-fat Pork | 65% |
| Pressed fungi mycelium | 15% |
| Salt | 2.2% |
| Nitrite | 0.01% |
| Sugar | 0.1% |
| Garlic | 0.1% |
| Pepper | 0.2% |

They are made according to the technology for perishable sausages.

EXAMPLE 2

| Preparation of Non-Perishable Sausages with Fungus Mycelium | |
|---|---|
| Ingredient | Amount |
| Semi-fat pork | 40% |
| Beef | 43% |
| Pressed fungi mycelium | 15% |
| Salt | 2.2% |
| Pepper | 0.3% |

They are prepared in the technology for non-perishable sausages.

EXAMPLE 3

| Processed Cheese with Fungus Mycelium | |
|---|---|
| Ingredient | Amount |
| Cheese | 30% |
| "Cheddar" cheese | 30% |
| Curds | 18% |
| Pressed fungi mycelium | 15% |
| Butter | 4% |
| Emulsified salts | 3% |
| Pepper | 0.3% |

The products were prepared according to the technology for processed cheeses.

EXAMPLE 4

| Vegetable Paste with Fungus Mycelium | |
|---|---|
| Ingredient | Amount |
| Pressed fungus mycelium | 20% |

-continued

| Vegetable Paste with Fungus Mycelium | |
|---|---|
| Ingredient | Amount |
| Peas | 12% |
| Blanched celery roots | 8% |
| Blanched parsnip | 8% |
| Blanched carrots | 10% |
| Marinated cucumbers | 10% |
| Pepper puree | 8% |
| Onion | 2% |
| Overheated cooking oil | 8% |
| Vinegar | 8% |
| Salt | 1% |
| Pepper | 0.06% |
| Water | 9% |

All components are minced, mixed and homogenized and thereafter sterilized.

EXAMPLE 5

| Fungus Soup | |
|---|---|
| Ingredient | Amount |
| Fungus flour | 10% |
| Dry fungus mycelium (flour) | 30% |
| Farina | 20% |
| Flour | 16% |
| Dried carrots | 2.8% |
| Dried parsley | 1.2% |
| Dried Celery | 0.8% |
| Powdered milk | 9% |
| Pepper | 0.1% |
| Monosodium glutamate | 0.2% |
| Salt | 10% |

All components were well homogenized, and the mixture packed in suitable bags of 50 g each.

EXAMPLE 6

The mother liquors are diluted 20–30 fold and then plants are watered with them. The watering is best done in a shower, so that the stimulating substances can be absorbed not only by the root system but also by the leaf system. The vegetables watered are mainly tomatoes, peppers, and cucumbers, grown in hot-houses, where the regime of watering can be controlled. The waterings numbered about 15 and start at the budding stage and go on into the mass picking stage.

The effect of stimulating these vegetables with mother waters raises the index of early ripening up to 5% in the first 10 pickings and raises the total output by about 15%.

What is claimed is:

1. A method for obtaining mycelium from a strain of polyporus genus selected from the group consisting of cultivated fungi having essentially all the characteristics of *Polyporus squamosus*-PS 64-103 and PS 24-44 and *Polyporus brumalis* PB 33-48, which comprises submerged cultivation of said strain of fungi on a nutrient media containing carbohydrate, nitrogen and phosphorus sources and then harvesting said mycelium.

2. The method of claim 1, wherein said fungi are cultivated at a temperature of 22° to 50° C., a pH from 4.5 to 7.5 and air from 0.6 $m^3$ to 1.2 $m^3$ per each 1 $m^3$ of nutrient media per minute.

3. The method of claim 1 wherein said fungi are cultivated at a volume of 2 $m^3$ in the course of a twenty-four hour time cycle, at a volume of 20 $m^3$ in an eighteen hour cycle, and in three growth cycles in progressively greater volumes of nutrient media contained in separate fermentation vessels, with the proviso that the first cycle involves a nutrient media volume of 2 $m^3$ and a 24 hour time period, the second cycle involves a nutrient media volume of 20 $m^3$ and a time period of 18 hours, and the third cycle involves a nutrient media volume of 100 $m^3$ and a time period of 6 hours, and with the further proviso that 50% of the volume of the cultivation media is separated and removed at the end of each cycle and the fungal mycellia being harvested at intervals during the cycles is continuously repeated every six hours, the fungi mycelium being harvested at intervals during said time cycle.

4. A method for obtaining mycelium from a strain of polyporus genus selected from the group consisting of cultivated fungi having essentially all the characteristics of *Polyporus squamosus*-PS 64-103 and PS 24-44 and *Polyporus brumalis* PB 33-48, which comprises submerged cultivation of said strain of fungi on a nutrient media containing carbohydrate, nitrogen and phosphorus sources at a temperature of 22° to 50° C., a pH from 4.5 to 7.5, and 1 $m^3$ of nutrient media per minute, whereby there is a rapid increase in the protein concentration of the fungi mycelium, and afterward isolating said mycelium.

5. The method of claim 4 wherein a semi-continuous method of cultivation is used in which one-tenth of the volume of the initial fermentation is retained as an inoculate and the cultivation is completed in 14 hours.

6. The method of claim 4 wherein said mutant strains are cultivated in a nutrient media containing 3 to 5% molasses, 1.10 to 0.20% ammonium nitrate, 0.08 to 0.15% potassium phosphate ($KH_2PO_4$), and 0.02 to 0.06% of a foam supressor.

* * * * *